United States Patent [19]

Babson

[11] Patent Number: 4,559,052
[45] Date of Patent: Dec. 17, 1985

[54] MULTIPLE USE CONTAINER FOR THE PACKAGING OF FLUIDS

[76] Inventor: Arthur L. Babson, Old Mill Rd., Chester, N.J. 07930

[21] Appl. No.: 581,313

[22] Filed: Feb. 17, 1984

[51] Int. Cl.⁴ .................... A61M 3/00; A61M 5/00; B65D 41/34
[52] U.S. Cl. .................................. 604/403; 604/415; 604/905
[58] Field of Search ................. 604/403, 415

[56] References Cited

U.S. PATENT DOCUMENTS 4,294,250 10/1981 Dennehey .................. 604/403
4,369,781 1/1983 Gilson et al. .............. 604/403
4,402,420 9/1983 Chernack .................. 604/403

Primary Examiner—Arthur P. Demers
Attorney, Agent, or Firm—George M. Yahwak

[57] ABSTRACT

Disclosed is a uniquely simple, multiple use apparatus for the packaging of fluids, such as those reference fluids used for the calibration and standardization of blood gas instrumentation, which must not be exposed to air.

7 Claims, 4 Drawing Figures

MULTIPLE USE CONTAINER FOR THE PACKAGING OF FLUIDS

The present invention relates in general to a uniquely simple, yet novel, multiple use container for the packaging of fluids, specifically those reference fluids used for the calibration and standardization of blood gas analyzers.

Blood gas analysis has provided the physician with a convenient analytical method for evaluating a patient's body metabolism and cardio-pulmonary system. This is accomplished by monitoring the laboratory determinations of the blood's pH, $PO_2$ (partial pressure of oxygen in the blood), and $PCO_2$ (partial pressure of carbon dioxide in the blood). The accurate measurement of $PO_2$ and $PCO_2$ in the blood of acute care patients is critical for successful respiratory therapy treatment of those patients, as relatively minor deviations from physiological pH, $PO_2$ and $PCO_2$ even for short periods of time can be life threatening. Thus the improvement in instrumentation have made the determination of blood pH, $PO_2$, and $PCO_2$ increasingly available to the medical technologist. Since vigorous therapeutic treatment is often dictated by test results, accuracy is essential. Accordingly, the use of control materials to verify the reliability of instrumentation and to provide an immediate indication of unexpected analytical deviations is important.

In the past, control materials to verify the reliability of blood pH, $PO_2$, and $PCO_2$ instruments had to be made by the medical technologist immediately prior to performing the test functions. Generally, this involves the adding of known quantities of oxygen and carbon dioxide gases to a Tonometer which contained a control sample liquid at a fixed pH. The gases and the liquid were equilibrated within the Tonometer, and an aliquot sample was removed carefully by the technician for callibrating, the blood gas instrumentation. As a result of the meticulous work involved and the necessity of specific gas mixtures, this procedure had been performed previously only in laboratories conducting research in the blood gas field.

Stability has also been lacking in prior control materials. Exposure of the control materials to air immediately begins to effect $PO_2$ and $PCO_2$ values. Clinical control materials containing protein are subject to bacterial contamination which causes immediate lowering of $PO_2$ values and increases $PCO_2$ values.

This instability of blood gas control solutions has long been recognized even in "improved" blood gas control solutions such as those disclosed in U.S. Pat. Nos. 4,001,142 to James E. Turner, and 4,299,728 to Alan D. Cormier, Marvin Feil, and Kenneth D. Legg. These "improved" blood gas control fluids may be packaged in the multiple use container of the present invention, and the stability and integrity of the solutions maintained.

A number of attempts have also been made to package blood gas control solutions in containers which would provide the stability to allow extended shelf life of the fluid. Two such attempts are described in U.S. Pat. Nos. 4,116,336 to Soren K. Sorensen and Carl. C. Holbek, and 4,266,941 to Kevin J. Sullivan. While both devices extend the useful shelf life of the fluid, neither device is as simple to manufacture, simple to use, and as highly efficient as that of the present invention. As for the "improved" blood gas control solutions mentioned previously, the solutions of these two patents may also be used in my multiple use container with greatly enhanced shelf life and ease of use.

By multiple use, I refer to a container which may be reopened and resealed a number of times without disrupting the chemical integrity of the blood gas control fluids container therein.

It is therefore an object of the present invention to describe a multiple use container for the packaging of fluids, specifically blood gas control fluids.

The exact manner in which these and other objects of the invention are achieved will become apparent when reference is made to the following detailed description of the preferred embodiments of the invention and the accompanying drawings in which like reference numerals indicate corresponding parts throughout the several views of the drawings.

IN THE DRAWINGS

Figure 1:
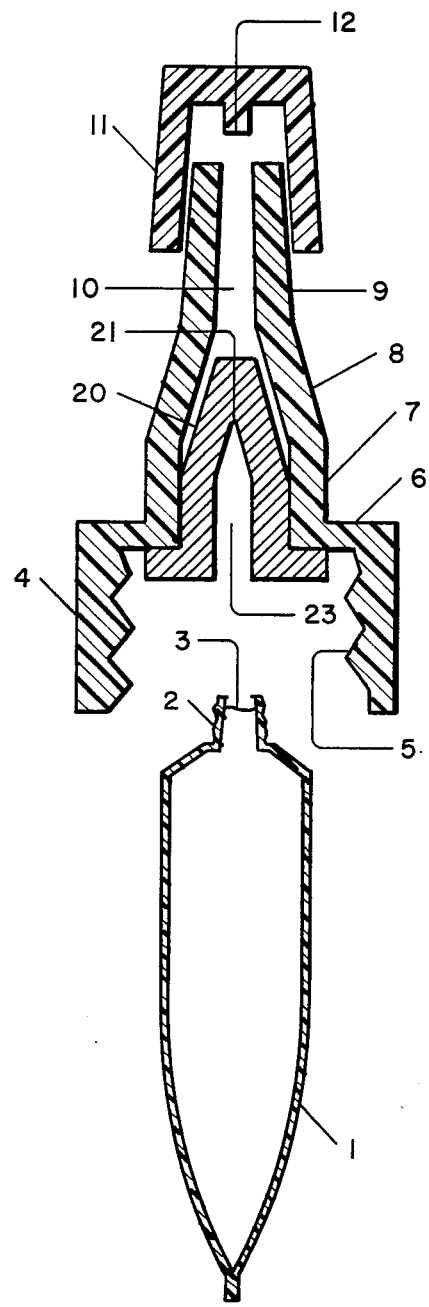
FIG. 1 is an exploded perspective cross sectional view, with the upper cap porton being shown enlarged, of the multiple use container according to the present invention.
Figure 2:
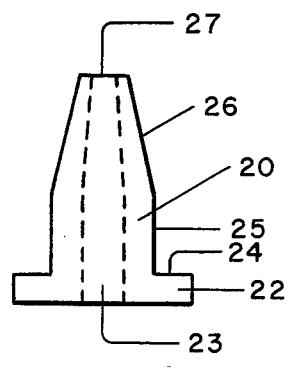
FIG. 2 is a side elevational view of the one-way valve contained in the cap portion of the multiple use container.

Referring to the drawings, and specifically to FIG. 1, the multiple use container of my invention is seen to consist of a collapsible dispensing tube 1, having a neck portion which carries a series of male threads 2 located at one end and an opposite "bottom" portion which is sealed by a crimp or other commonly employed means.

When manufactured, collapsible dispensing tube 1, which is shown in vertical cross section as a squeeze tube container similar in shape to those tubes conventionally used for the packaging of dental creams or cosmetic preparations as disclosed in U.S. Pat. No. 4,261,482, for example, will contain a fluid for the calibration and standardization of blood gas instrumentation. These fluids may be, for example, those as disclosed in U.S. Pat. Nos. 4,004,142; 4,116,336; or 4,299,728. Each of these fluids requires their respective chemical integrities to be maintained in order for valid readings of blood pH, $O_2$ and $CO_2$ to be obtained. In order to prevent the fluid contained in the squeeze tube container from being exposed to the air, which would be detrimental to the integrity of the fluid, the opening found in the neck of the container is sealed with a puncturable seal 3 which is impervious to air, and which may be manufactured as a foil of the same, or different, material as the vessel; the requirements being that the seal be impervious to air, nonreactive to the contents of the vessel, and easily puncturable by the technician.

Cap portion 4 having a central axial opening extending therethrough is adapted to fit over the opening of the collapsible dispensing tube 1 by threading sealing cap 4 onto tube 1 and allowing the male threads 2 on the tube neck to engage the female threads 5 carried on the inner surface of the cap.

Cap 4 consists of an annular cylindrical body portion having an inner surface carrying female threads 5, in which the body is sized and adapted to fit about the neck of the collapsible dispensing tube. The body portion carries an upper reducing disc 6 which sufficiently reduces the inner diameter of the cylindrical body to allow for the insertion of a single direction valve means 20 to fit within the control interior passageway of the cap 4, and to form an air-tight gasket seal about annular disc ring 22 carried by valve means 20, with the most distal end of the tube 1 neck portion when cap 4 is tightly secured to the collapsible dispensing tube 1, thereby forming a gas tight seal between the upper surface 24 of means 20, and the central inner surface of the cap 4.

Valve means 20 may be, for examle, what is commonly referred to as a duck-bill valve comprising an outer nipple 25, an adjacent tapered front piece 26 terminating in a forward rectangular end plane 27. Plane 27 carries a tightly sealed opening slit 21 which communicates with channel 23 extending longitudinally through said duck-bill.

Forward of the reducing disc 6 is an upwardly extending mid-piece 7, an inwardly-tapered conical front piece 8, and a leur tip 9. Leur tip 9 is unique in that such a taper, will allow a device, such as a hypodermic needle to slip over the leur tip. Because of the leur tip 9, the container is especially adapted to inject the contained blood gas control fluid into the input port of a blood gas analyzer; a procedure that has previously required the technician to aspirate the control fluid into a syringe, remove the hypodermic needle from the syringe, and place the leur tip of the syringe into the input port of the analyzer.

With the cap 4 of the present invention, all one has to do is puncture the seal 3, tighten cap 4 on the neck of the collapsible tube 1, remove the sealant cap 11, and collapse tube 1 to dispense the desired amount of gas control fluid through unidirectional valve means 20 and axial dispensing passageway 10 into the input port of the blood gas analyzer.

After the desired amount is dispensed, the sealant cap 11 is replaced on the cap 4, and the tube put away until additional fluid is required. Because of the unidirectional valve means 20, the tighting fitting sealing cap 11, and the partially collapsed tube 1, the fluid contents of the tube will be effectively gas sealed thereby maintaining the chemical integrity of the fluid.

As is depicted in FIG. 1, sealant cap 11 will fit tightly over leur tip 9 (the internal taper of cap 11 is equal to the leur taper of tip 9), and the rearwardly disposed central plug 12 carried by cap 11 will fiction-fit into the end opening of leur tip 9.

Figure 3:
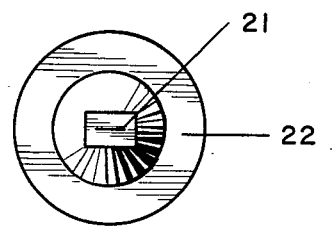
FIG. 3 is a plan view of the upper surface of the one-way valve.
Figure 4:
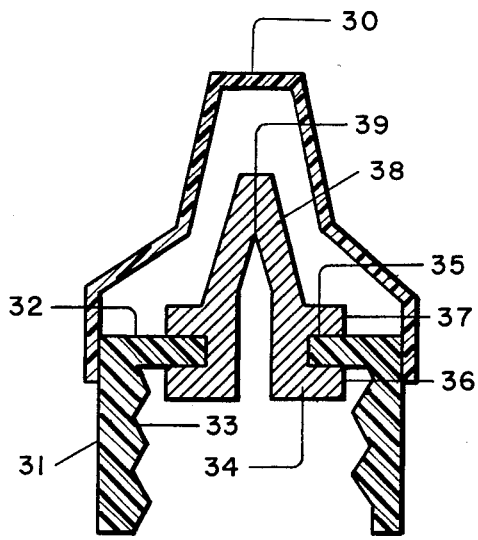
FIG. 4 is a vertical cross-sectional view of another embodiment of the cap portion of the multiple use container.

An alternative cap means is depicted in FIG. 3 wherein the body 31 of the screw-on cap terminates in a flat disc 32 having a central opening through which a unidirectional valve means 34 is positioned. The valve means 34 has a grommet base piece having a forward 37 and rearwardly 36 grommet seal adapted to be snap-fitted 35 about disc 32. As with the base of the unilateral valve means of FIG. 1, valve means 34 is also adapted at this rear surface 34 to form a gas-tight seal when the cap is threaded onto the neck of collapsible tube 1 and the female threads 33 carried by the cap are contacted with those male threads 2 carried on the neck of the tube. This modification is also unique in that the forward end of valve 34 is itself a leur taper tip 38 which will, when fluid is dispersed through opening 39, form a gas tight seal with the interior of the input port of the blood gas analyzer. Over this cap assembly is a sealant cap 30 which may be of any design provided it forms a firction fit juncture with the body of cap 31 and protects the unidirectional valve means.

Thus, while I have illustrated and described the preferred embodiment of my invention, it is to be understood that this invention is capable of variation and modification, and I therefore do not wish to be limited to the precise terms set forth, but desire to avail myself of such changes and alterations which may be made for adapting the invention to various usages and conditions. Accordingly, such changes and alterations are properly intended to be within the full range of equivalents, and therefore within the purview, of the following claims.

Having thus described my invention and the manner and process of making and using it, in such full, clear, concise, and exact terms so as to enable any person skilled in the art to which it pertains, or with which is it most nearly connected, to make and use the same:

I claim:

1. A multiple use container for blood gas control fluids comprising a gas impermeable collapsible tube; a blood gas control fluid within said tube; a cap adapted to fit over a neck portion of said tube; a unidirectional valve means positioned in said cap, said valve means being gas impermeable when closed; and said cap terminating in a leur tip.

2. The multiple use container of claim 1 wherein the neck portion of said tube is sealed with a puncturable seal said seal being impervious to air.

3. The multiple use container of claim 1 wherein the unidirectional valve means is a duck-billed valve.

4. A multiple use container comprising a gas impermeable collapsible tube; a cap adapted to fit over a neck portion of said tube; a unidirectional valve means positioned in said cap, said valve means being gas impermeable when closed; and said cap terminating in a leur tip.

5. A cap adapted to fit over the opening of a container to selectively seal said container, said cap having a unidirectional valve means positioned in said cap, said means being gas impermeable when closed, and said cap terminating in a leur tip.

6. The cap according to claim 5 wherein the unidirectional valve means is a duck-billed valve.

7. The multiple use container of claim 4 wherein the neck portion of said tube is sealed with a puncturable seal, said seal being impervious to air.

* * * * *